US00PP11964P2

(12) United States Plant Patent
Hoek

(10) Patent No.: US PP11,964 P2
(45) Date of Patent: Jun. 26, 2001

(54) CHRYSANTHEMUM PLANT NAMED 'DELISTAR'

(75) Inventor: Jan Hoek, Gravenzande (NL)

(73) Assignee: Deliflor Chrysanten B.V., Maasdijk (NL)

( * ) Notice: Subject to any disclaimer, the term of this patent is extended or adjusted under 35 U.S.C. 154(b) by 0 days.

(21) Appl. No.: 09/334,023

(22) Filed: Jun. 15, 1999

(51) Int. Cl.[7] ..... A01H 5/00
(52) U.S. Cl. ..... Plt./288
(58) Field of Search ..... Plt./288

*Primary Examiner*—Howard J. Locker
(74) *Attorney, Agent, or Firm*—C. A. Whealy

(57) ABSTRACT

A distinct cultivar of Chrysanthemum plant named 'Delistar', characterized by its quilled spider-type double inflorescences that are about 8 to 11 cm in diameter with white ray florets; inflorescences that consist mostly of ray florets and few disc florets which are typically inconspicuous; dark green foliage; strong flower stems; low number of lateral branches, advantageous for disbudding; early response time, plants flower after about seven weeks of photoinductive treatments; not attractive to leafminers; excellent postproduction longevity; suitability for coloring (dying); and tolerance to low light conditions.

1 Drawing Sheet

BACKGROUND OF THE INVENTION

The present invention relates to a new and distinct cultivar of Chrysanthemum plant, botanically known as *Dendranthema grandiflora* and referred to by the cultivar name Delister.

The new Chrysanthemum is a product of a planned breeding program conducted by the Inventor in 's-Granvenzande, The Netherlands. The objective of breeding program was to create new cut Chrysanthemum cultivars having double spider-type inflorescences with white ray florets, unattractive to leafminers (*Lyriomyza trifolii*) and with good inflorescence form and substance.

The new Chrysanthemum originated from a cross made by the Inventor in the Autumn of 1996, in 's-Gravenzande, The Netherlands, of the *Dendranthema grandiflora* cultivar Spider White, not patented, as the female, or seed, parent with a proprietary Chrysanthemum selection identified as code number 94816, as the male, or pollen, parent. Seed from the cross was sown on Jan. 28, 1998, and the cultivar Delistar was discovered and selected by the Inventor within the progeny of the stated cross in a controlled environment in 's-Gravenzande, The Netherlands, on or about May 27, 1998.

The selection of this plant was based on its inflorescence form, color and good substance.

Asexual reproduction of the new Chrysanthemum by terminal cuttings harvested in 's-Gravenzande, The Netherlands, has shown that the unique features of this new Chrysanthemum are stable and reproduced true to type in successive generations.

BRIEF SUMMARY OF THE INVENTION

The cultivar Delistar has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Delistar'.

These characteristics in combination distinguish 'Delistar' as a new and distinct cultivar:

1. Quilled spider-type double inflorescences that are about 8 to 11 cm in diameter with white ray florets.
2. Inflorescences consist mostly of ray florets and few disc florets which are typically inconspicuous.
3. Dark green foliage.
4. Strong flower stems.
5. Low number of lateral branches, advantageous for disbudding.
6. Early response time; plants flower after about seven weeks of photoinductive treatments.
7. Unattractive to leafminers.
8. Excellent postprodction longevity and tolerates transport well.
9. Suitable for coloring (dying).
10. Tolerant to low light conditions; can be grown without the benefit of supplemental lighting.

Plants of the new Chrysanthemum differ from plants of the female parent, the cultivar Spider White, in the following characteristics:

1. Leaves of plants of the new Chrysanthemum are darker green, broader at the base and have shorter petioles than leaves of plants of the cultivar Spider White.
2. Plants of the new Chrysanthemum flower at least seven days earlier than plants of the cultivar Spider White.
3. Plants of the new Chrysanthemum flower have fewer inflorescences per stem and therefore more suitable for growing as a disbud than plants of the cultivar Spider White.
4. Ray floret corolla tubes of plants of the new Chrysanthemum are more than ray floret corolla tubes of plants of the cultivar Spider White.
5. Inflorescences of plants of the new Chrysanthemum develop few noticeable disc florets whereas inflorescences of plants of the cultivar Spider White develop noticeable green disc florets.

Plants of the new Chrysanthemum differ from plants of the male parent, the selection 94816, in the following characteristics:

1. Leaves of plants of the new Chrysanthemum are not as erect as leaves of plants of the selection 94816.
2. Plants of the new Chrysanthemum are less freely branching than plants of the selection 94816.
3. Ray florets of plants of the new Chrysanthemum are tubular whereas ray florets of plants of the selection 94816 are flat.
4. Inflorescences of plants of the new Chrysanthemum develop few noticeable disc florets whereas inflorescences of plants of the selection 94816 develop numerous disc florets.
5. Anthers of plants of the new Chrysanthemum produce much less pollen than anthers of plants of the selection 94816.

BRIEF DESCRIPTION OF THE PHOTOGRAPH

The accompanying colored photograph illustrates the overall appearance of the new cultivar, showing the colors as true as it reasonably possible to obtain in colored reproductions of this type. The photograph comprises a view of a typical inflorescence of 'Delistar'. Floret and foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary signficance are used. The folowing observations and measurements describe plants grown in 's-Gravenzane, The Netherlands, under commercial practice in a glass-covered greenhouse. Plants were initially given short nyctoperiods followed by long nyctoperiods to induce flower initiation and development. Average day and night temperatures were 18 and 19° C., respectively.

Botanical classification: *Dendranthema grandifora* cultivar Delistar.

Commercial classification: Quilled spider-type double Chrysanthemum typically grown as a cut flower.

Parentage:

*Male or pollen parent.*—Unnamed proprietary *Dendranthema grandiflora* selection identified as code number 94816.

*Female or seed parent.*—*Dendranthem grandiflora* cultivar Spider white, not patented.

Propagation:

*Type.*—Terminal tip cuttings.

*Time to initiate roots, summer.*—About 10 days at 20° C.

*Time to initiate roots, winter.*—About 14 days at 20° C.

*Rooting habit.*—Root initiation and development is rapid. Roots are fine, fibrous and well-branched.

Plant description:

*Appearance.*—Herbaceous quilled spider-type cut Chrysanthemum; typically grown as a disbud. Upright with strong stems.

*Growth rate.*—Moderate; moderately vigorous.

*Crop time.*—For cut flowers, about 78 and 117 days are required to produce flowering stems during the summer and winter, respectively.

*Stem description.*—Length: About 70 to 80 cm. Strength: Strong. Aspect: Upright. Color: 146C. Number of lateral branches: Not very freely branching, about 8 to 12; low branching is advantageous for disbud culture. Lateral branch length: About 10 to 16 cm.

*Foliage description.*—Arrangement: Alternate. Quantity of leaves per main stem: About 11 to 13. Quantity of leaves per lateral stem: About 4. Length: About 10 to 14 cm. Width: About 8 to 11 cm. Apex: Acute. Base: Acute to rounded. Margin: Palmately lobed. Texture: Rough; both surfaces pubescent. Color: Young foliage, lower surface: 137B-137C. Young foliage, upper surface: 137A-137B. Mature foliage, upper surface: 137A-137B. Mature foliage, lower surface: 137C-137D. Venation, upper and lower surfaces: 137D. Petiole: Length: About 3 to 4 cm. Color: 137D.

Flowering description:

*Appearance.*—Quilled spider type double inflorescence form. Inflorescences borne on terminals, arising from leaf axils. Ray and disc florets arranged acropetally on the receptacle.

*Flowering response.*—Under natural conditions, plant typically flowers in November in the Northern Hemisphere. At other times of the year, inflorescence initiation and development can be induced under short day/long night conditions (at least 13.5 hours of darkness). Plants exposed to long day/short night conditions after planting following by photoinductive short day/long night conditions flower about seven weeks later.

*Postproduction longevity.*—Inflorescences will maintain good substance and form for about 3.5 weeks after harvesting.

*Quantity of inflorescences per flowering stem.*—About 6 to 9.

*Inflorescence size.*—Diameter: About 8 to 11 cm. Depth (height): About 4 to 5 cm. Diameter of disc: About 5 mm; typically inconspicuous.

*Inforescence buds.*—Length: About 1 to 1.5 cm. Diameter: About 1.2 to 1.5 cm. Shape: Flattened sphere to spherical.

*Ray florets.*—Length, fully developed: About 5 to 5.5 cm. Width, fully developed: About 4 to 5 mm. Shape: Quilled; fused, tubular. Texture: Smooth, glabrous. Number of ray florets per inflorescence: About 200. Color: When opening, upper and lower surfaces: 155D with a very slight green flush. Mature, upper surface: 155D. Mature, lower surface: 155D. Mature, base: 150C.

*Disc forets.*—Shape: Oblong, tubular. Length: About 4 mm. Width: About 1 mm. Number of disc florets per inflorescence: Few, about 25; typically inconspicuous. Color: Immature: Greenish white; no similar color found in R.H.S. Colour Chart. Mature: Apex: 13A. Base: Greenish white; no similar color found in R.H.S. Colour Chart.

*Peduncles.*—Length, terminal peduncle: About 8 to 10 cm. Length, fourth peduncle: About 13 to 15 cm. Diameter: About 2 to 3 mm. Angle: About 60 to 80° to main stem. Texture: Pubescent. Color: 137C–137D.

*Reproductive organs.*—Androecium: Present on disc florets only. Anther color: 15B. Pollen: 16B. Gynoecium: Present on both ray and disc florets. Stigma length: About 5 mm. Stigma width: About 0.5 mm. Stigma color: Apex: 9B. Base: Close to 150D.

Seed production: Seed prouction has not been observed.

Disease resistance: Resistance to known Chrysanthemum diseases has not been observed on plants of the new Chrysanthemum.

Insect attractiveness: Plant of the new Chrysanthemum have been shown to be unattractive to leafminers (*Lyriomyza trifolii*).

It is claimed:

1. A new and distinct cultivar of Chrysanthemum plant named 'Delistar', as illustrated and described.

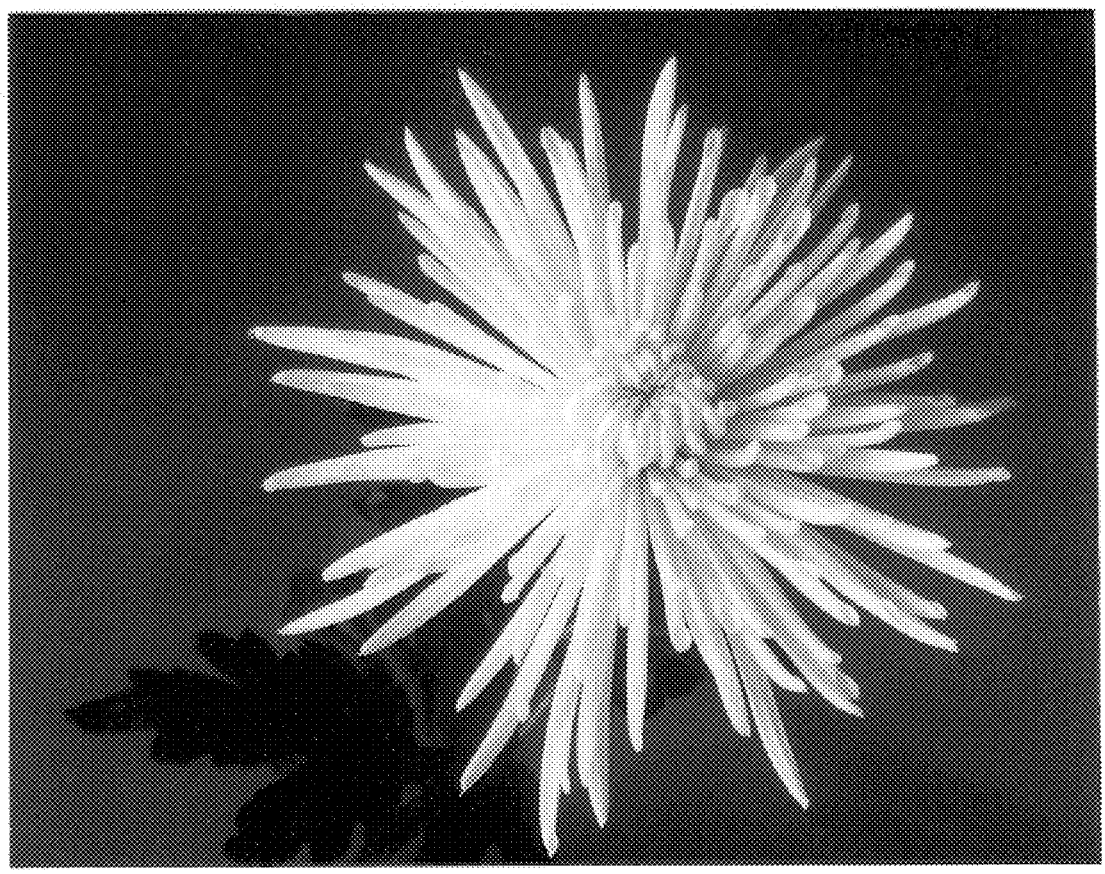

* * * * *